(12) United States Patent
Wolter et al.

(10) Patent No.: US 10,071,195 B2
(45) Date of Patent: Sep. 11, 2018

(54) METHOD AND SYSTEM FOR SUPPLYING RINSING SOLUTION DURING ENDOSCOPIC INTERVENTIONS

(71) Applicant: OLYMPUS WINTER & IBE GMBH, Hamburg (DE)

(72) Inventors: Michael Wolter, Hamburg (DE); Susanne Stahlkopf, Hamburg (DE); Marc Van Assche, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 910 days.

(21) Appl. No.: 14/482,103

(22) Filed: Sep. 10, 2014

(65) Prior Publication Data
US 2014/0378768 A1 Dec. 25, 2014

Related U.S. Application Data

(63) Continuation of application No. PCT/EP2013/000664, filed on Mar. 7, 2013.

(30) Foreign Application Priority Data

Mar. 23, 2012 (DE) .................. 10 2012 204 680

(51) Int. Cl.
*A61M 3/02* (2006.01)
*A61M 1/00* (2006.01)
(Continued)

(52) U.S. Cl.
CPC .......... *A61M 3/0233* (2013.01); *A61B 18/00* (2013.01); *A61M 1/0058* (2013.01); *A61B 18/12* (2013.01);
(Continued)

(58) Field of Classification Search
CPC .............. A61M 1/0058; A61M 3/0233; A61M 2205/70; A61B 2018/00744; A61B 2018/00863; A61B 1/015
See application file for complete search history.

(56) References Cited

U.S. PATENT DOCUMENTS

| 4,261,360 A | 4/1981 | Perez |
| 5,382,232 A * | 1/1995 | Hague .................. A61M 5/365 128/DIG. 13 |

(Continued)

FOREIGN PATENT DOCUMENTS

| CN | 1950125 B | 5/2010 | |
| DE | 4102843 C1 * | 5/1992 | .............. A61M 3/02 |

(Continued)

OTHER PUBLICATIONS

English abstract of EP 0497159 A1 dated Aug. 5, 1992.
(Continued)

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

A method for supplying rinsing solution during endoscopic interventions. The method including: conveying a rinsing solution by means of a rinsing solution pump from a rinsing solution supply to an endoscopic instrument to be introduced into the body cavity of a patient; and detecting at least one material characteristic of the rinsing solution by means of a measuring apparatus.

6 Claims, 3 Drawing Sheets

(51) Int. Cl.
  *A61B 18/00* (2006.01)
  *A61B 1/015* (2006.01)
  *A61B 18/12* (2006.01)

(52) U.S. Cl.
  CPC ............... *A61B 2018/00744* (2013.01); *A61B 2018/00863* (2013.01); *A61B 2218/002* (2013.01); *A61M 2205/18* (2013.01); *A61M 2205/3306* (2013.01)

(56) References Cited

U.S. PATENT DOCUMENTS

| | | | |
|---|---|---|---|
| 5,586,973 | A | 12/1996 | Lemaire et al. |
| 5,879,288 | A * | 3/1999 | Suzuki ............... A61B 1/00068 600/121 |
| 2004/0024380 | A1 | 2/2004 | Darnell et al. |
| 2005/0277890 | A1 | 12/2005 | Stewart et al. |
| 2008/0154095 | A1 | 6/2008 | Stubkjaer et al. |
| 2011/0071582 | A1 | 3/2011 | Willyard et al. |
| 2011/0270216 | A1 * | 11/2011 | Rykhus ............... A61M 5/1452 604/500 |
| 2011/0272016 | A1 | 11/2011 | De Ceuster et al. |

FOREIGN PATENT DOCUMENTS

| | | |
|---|---|---|
| DE | 4102843 C1 | 5/1992 |
| JP | H05-345023 A | 12/1993 |
| JP | H06-504221 A | 5/1994 |
| JP | H07-8456 A | 1/1995 |
| JP | H11-340186 A | 12/1999 |
| WO | WO 2011/019947 A1 | 2/2011 |

OTHER PUBLICATIONS

International Search Report dated Jun. 26, 2013 issued in PCT/EP2013/000664.

Chinese Office Action dated Jan. 27, 2016 from related Chinese Patent Application No. 201380015771.1, together with an English language translation.

Japanese Notification of Reasons for Refusal dated Feb. 20, 2018 received in Japanese Patent Application No. 2015-500789, together with an English-language translation.

* cited by examiner

METHOD AND SYSTEM FOR SUPPLYING RINSING SOLUTION DURING ENDOSCOPIC INTERVENTIONS

CROSS-REFERENCE TO RELATED APPLICATION

The present application is a continuation of PCT/EP2013/000664 filed on Mar. 7, 2013, which is based upon and claims the benefit to DE 10 2012 204 680.1 filed on Mar. 23, 2012, the entire contents of each of which are incorporated herein by reference.

BACKGROUND

Field

The invention relates to a method for supplying rinsing solution during endoscopic interventions in which a rinsing solution is conveyed by means of a rinsing solution pump from a rinsing solution supply to an endoscopic instrument for introduction into a body cavity of a patient, a system to supply rinsing solution for endoscopic interventions comprising a rinsing solution pump by means of which the rinsing solution can be conveyed from a rinsing solution supply to an endoscopic instrument, as well as a rinsing solution pump.

Prior Art

Corresponding endoscopic interventions in which a rinsing solution is used to fill a body cavity are for example urological diagnostics or urological interventions, for example with resectoscopes, in which body tissue is removed and the wound is cauterized with a current-carrying wire noose or wire loop. These also include high-frequency applications, so-called HF applications, in which a high-frequency electro-magnetic alternating field generated by a HF generator within a frequency range of a few hundred kilohertz to approximately 1 MHz is used.

To supply rinsing solution, irrigation pumps, normally peristaltic pumps, are used in which a flexible hose is subdivided into individual chambers on the perimeter of the rolling wheel by means of a rolling wheel with bodies distributed over the perimeter, or suitable other means, and the chambers are completely separated from each other by means of the moving bodies. Since the chambers move as the rolling wheel moves, rinsing solution is drawn through the hose from a rinsing solution supply and conveyed to an endoscopic instrument, and the rinsing solution passes through its shaft into the body cavity.

Rinsing media which are frequently used are saline solutions or electrolyte-free solutions such as Purisole®. Purisole®, which can be obtained from Fresenius, is a solution of mannitol and sorbitol in water. Glycol solutions are also suitable for this use. Saline solutions are sodium chloride solutions that for example can have a content of 0.9% w/v. The difference between rinsing solutions is insignificant in diagnostics. If, however, current or high-frequency technology is used, the solution plays a decisive role due to its different conductivity.

In the case of monopolar HF applications, a ground electrode or neutral electrode is placed covering a large area on the body of the patient to avoid local skin burns, whereas on the tip of the endoscope shaft, a monopolar high-frequency electrode is arranged at which a high flow of current predominates and which is used for the intervention. In this case, an electrolyte-free solution must be used that ensures reliable current conduction to the tissue and hence a good connection to the neutral electrode.

In the case of bipolar HF applications, the two poles of the HF electrode are on the distal tip of the endoscope shaft. In this case, a saline solution must be used. These provide a favorable flow of current between the poles at the tip of the electrode.

The surgeon and the surgical staff must make sure that the correct solution is used and no mix-ups occur which could lead to the patient being harmed.

SUMMARY

In comparison with the prior art, an object of the present invention is to avoid patient harm and provide an option by means of which use of an unsuitable rinsing solution for the endoscopic intervention to be performed is reliably avoided.

This object is achieved by means of a method for supplying rinsing solution during endoscopic interventions in which a rinsing solution is conveyed by means of a rinsing solution pump from a rinsing solution supply to an endoscopic instrument to be introduced into the body cavity of a patient, the method being developed in that at least one material characteristic of the rinsing solution is detected by means of a measuring apparatus. According to the invention, it is no longer only the job of the surgical staff or surgeon to make sure that the correct solution is used. An option exists of monitoring with an instrument by measuring a material characteristic, or several material properties, of the rinsing solution. This measuring establishes the groundwork for being able to undertake additional measures if an employed rinsing solution for the planned intervention is unsuitable, and to identify rinsing solution mix-ups.

In one embodiment, a conductivity measurement and/or a capacitive measurement of the rinsing solution is/are performed by the measuring apparatus, in particular with a low-frequency alternating voltage. The conductivities of the rinsing solutions that are normally used, saline and electrolyte-free solutions, differ so strongly that a local test with weak current which does not endanger the patient can yield reliable results and enable a distinction between the rinsing solutions. The permittivities of the different rinsing solutions, for example between saline and glycol, also differ by an order of magnitude so that a capacitive test in which for example two capacitor surfaces are used between which the hose is arranged in which the rinsing solution is conducted, leads to significantly different measuring results in regard to the capacity of the capacitor formed in this manner. In particular, a measurement with low-frequency alternating voltage can occur, wherein a phase shift changes between the current and voltage. Within a range of a few kHz to a few 100 kHz, the ionic conductivity has a measurable influence that decreases at higher frequencies. In this manner, discrimination between the rinsing solutions is reliably possible. The two measuring methods can also be combined with each other to achieve greater reliability.

Alternately or in addition, an optical measurement of the rinsing solution is preferably performed by means of the measuring apparatus, in particular on the basis of a light refraction, a total reflection or an absorption of UV light, visible or infrared light. Within the context of the invention, the different measuring methods can be performed in one measuring apparatus, or a plurality of measuring apparatuses. The optical measuring version also uses different material properties of the different rinsing solutions. The refraction index or the optical density of the rinsing solutions is accordingly different. For example, emitted light is refracted differently in different media. The different light refraction is a distinct distinguishing feature. This can also be used to adjust a measuring apparatus such that total reflection for one rinsing solution occurs at a boundary layer, such as with a glass plate, whereas such a total reflection does not occur in the other rinsing fluid. In this manner, the measurement of whether or not the emitted light passes through the glass plate clearly indicates whether one or the other rinsing liquid is at issue. The calculation of the total reflection angle is known to a person skilled in the art.

The different solutions also differ in terms of the absorption properties, in particular within the infrared spectrum. UV radiation or infrared radiation can be used in this case as a test radiation at which one of the solutions manifests stronger absorption and the other does not.

It is provided alternately or in addition to the aforementioned measurements that an acoustic measurement of the rinsing solution is performed by means of the measuring apparatus, in particular using ultrasound. An acoustic measurement in particular constitutes introducing sound of one or more frequencies into the rinsing solution and recording the sound at a different location. The frequency spectrum and/or noise level is then determined. Since for example a glycol solution is more viscous than a saline solution, greater attenuation occurs in the glycol solution. If several different frequencies are used which are analyzed separately, the relation of attenuations or noise levels of the different frequencies to each other can provide information on the type of rinsing solutions used since the absorption in a liquid generally rises with the square of the frequency. In the case of a weakly absorbing medium, the attenuation will therefore be scarcely different at different frequencies whereas the relationship of the noise levels at higher frequencies to the noise levels at lower frequencies develops very differently in more viscous liquids.

Alternately, phase shifts of the incoming noise can be evaluated that arise from the different speed of sound in the media. A resonance measurement can also be performed. A resonance chamber can be used through which the rinsing solution flows, and into which a sound is introduced at a frequency that resonates in the resonating chamber for a type of rinsing solution, whereas no resonance forms in the other media due to the difference exit speed of sound.

The type of rinsing solution can be determined in an evaluation apparatus from the at least one measured material characteristic, and/or it is tested whether the rinsing solution is suitable for an intervention that has been performed or is to be performed with the endoscopic instrument. The type of intervention to be performed or that has been performed can either be entered manually into the evaluation apparatus or the HF generator, or can result from a computer system, such as an operation guidance system, that contains all of the essential information about the intervention to be performed, or in which the evaluation apparatus is linked to the endoscopic instrument or its control apparatus, and which type of intervention should be performed is hence discernible from the type of instrument or its mode.

A warning signal can be emitted and/or a health-endangering supply of current from parts of the endoscopic instrument is interrupted if the rinsing solution is unsuitable for the intervention. This concerns particularly the HF generator. In this manner, the situation is avoided in which there is no warning, or a health-endangering intervention is continued if an incorrect rinsing solution is used for an intervention. To date, this has only been noticed when problems arose with the employed resection technique or HF technique. At that time, patient endangerment was already acute, or the patient was already injured.

The surgeon or surgical staff is warned by the emission of an optical and/or acoustic warning signal and/or a vibration signal and can decide which measures must be pursued to treat the patient. This can for example only mean exchanging a rinsing solution and washing out the wrong rinsing solution from the body cavity of the patient, or complete termination of the intervention. If the health-endangering power supply is interrupted from parts of the endoscopic instrument, particularly the HF supply to the HF probe, or the power supply to the wire loop of a resectoscope, direct endangerment to health is also terminated immediately. In this manner, risk to the patient is prevented from using an incorrect rinsing solution without direct monitoring by the surgeon or surgical staff, in particular preferably in addition thereto.

The above-identified object of the invention is also achieved by a system for supplying rinsing solution in endoscopic interventions comprising a rinsing solution pump by means of which the rinsing solution can be conveyed from a rinsing solution supply to an endoscopic instrument, the system being developed in that a measuring apparatus is included which is designed to detect at least one material characteristic of the rinsing solution. By means of this system, particularly the above-described method according to the invention can be implemented. By means of this system, the danger to the patient from using an incorrect or unsuitable rinsing solution for the planned intervention can be minimized.

The measuring apparatus is preferably provided as an electric measuring apparatus, capacitive measuring apparatus, optical measuring apparatus and/or an acoustic measuring apparatus. A plurality of measuring apparatuses can also be used next to each other to measure different material properties.

An evaluation apparatus can be included which is designed to determine the type of rinsing solution from the at least one measured material characteristic, and/or to test whether the rinsing solution is suitable for an intervention to be performed or that has been performed by the endoscopic instrument, wherein in particular the evaluation apparatus is connectable or connected to the endoscopic instrument and is designed to determine the type of required rinsing solution by identifying the endoscopic instrument or its mode, and/or to test whether the rinsing solution is suitable for an intervention to be performed, or that has been performed, by means of the endoscopic instrument. The evaluation apparatus is preferably designed to emit a warning signal when the identified rinsing solution does not correspond to the required solution, and/or to control an HF generator to interrupt a health-endangering power supply to parts of the endoscopic instrument.

In one embodiment, it is provided that the measuring apparatus and/or the evaluation apparatus is or are integrated in the rinsing solution pump and/or is or are arranged in or on the rinsing solution pump. The emission of warning signals, measurement of the material properties of the solution and the logic of the system and method according to the invention are hence concentrated at a central location, i.e., in the rinsing solution pump so that, for example, when a warning signal sounds, it is immediately discernible that there is a problem with an unsuitable rinsing solution.

Finally, the object can also be achieved by a rinsing solution pump for supplying rinsing solution in endoscopic interventions, in particular in a or for a previously described system according to the invention which is developed in that a measuring apparatus is included which is designed to detect at least one material characteristic of the rinsing solution, wherein the measuring apparatus is in particular provided as an electric, capacitive, optical and/or acoustic measuring apparatus.

An evaluation apparatus can be included which is designed to determine the type of rinsing solution from the at least one measured material characteristic, and/or to test whether the rinsing solution is suitable for an intervention to be performed or that has been performed by the endoscopic instrument, wherein in particular the evaluation apparatus is connectable or connected to the endoscopic instrument and is designed to determine the type of required rinsing solution by identifying the endoscopic instrument or its mode.

The evaluation apparatus is designed to emit a warning signal when the identified rinsing solution does not correspond to the required solution, and/or to control an HF generator to interrupt a health-endangering power supply to parts of the endoscopic instrument.

The system according to the invention and the rinsing solution pump according to the invention are provided and suitable for implementing the above-described method according to the invention. All the advantages, features and properties of the subjects of the invention, i. e. the method, system and rinsing solution pump, also apply to the other subjects of the invention which relate to different aspects of the same invention.

Further features of the invention will become apparent from the description of the embodiments according to the invention together with the claims and the included drawings. Embodiments according to the invention can fulfill individual features or a combination of several features.

BRIEF DESCRIPTION OF THE DRAWINGS

The invention is described below, without restricting the general idea of the invention, using exemplary embodiments with reference to the drawings, whereby we expressly refer to the drawings with regard to the disclosure of all details according to the invention that are not explained in greater detail in the text. In the figures.

DETAILED DESCRIPTION

Figure 1:
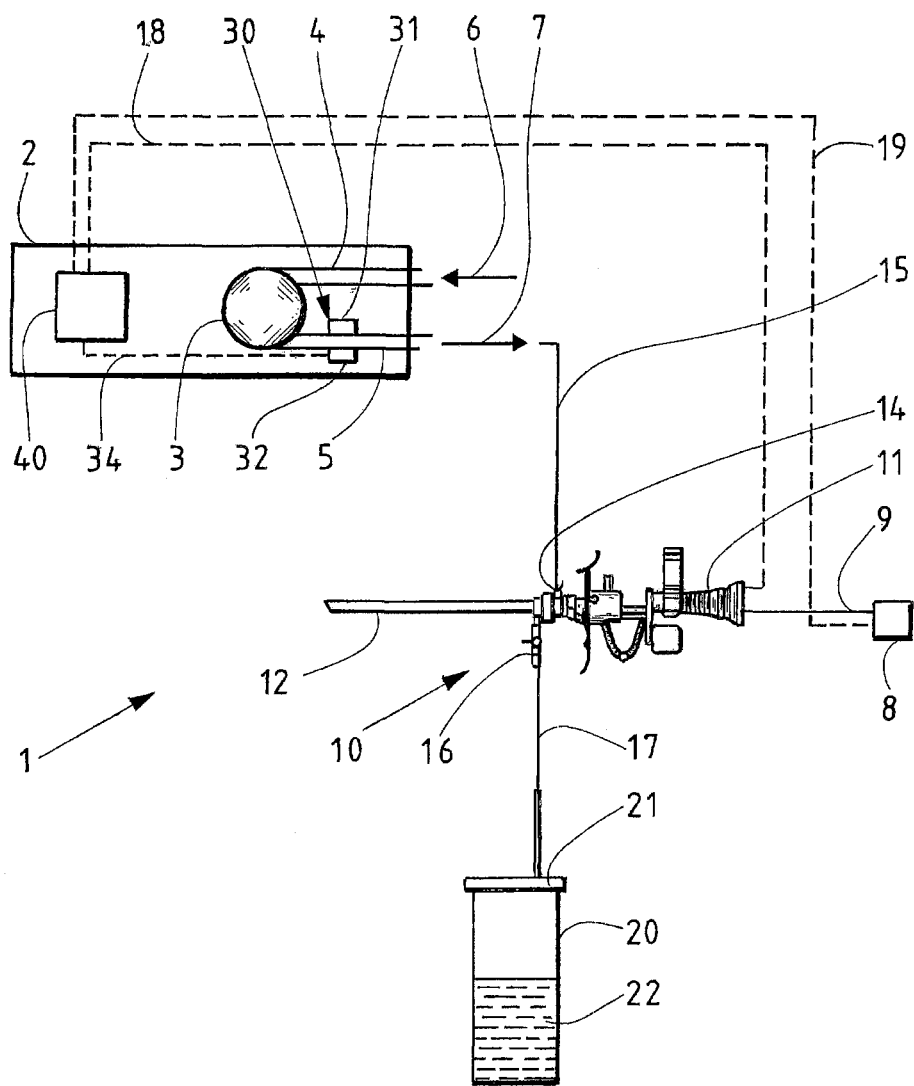
FIG. 1 illustrates a schematic representation of a system according to the invention, FIGS. 2a) and 2b) illustrate infrared absorption spectra of saline solution and glycols.

In the drawings, the same or similar types of elements and/or parts are provided with the same reference numbers in order to prevent the item from needing to be reintroduced.

FIG. 1 schematically portrays a system 1 according to the invention for supplying rinsing solution during endoscopic interventions. The central element of the embodiment according to FIG. 1 is a rinsing solution pump 2 which is based on the principle of peristaltic pumps. The rinsing solution pump 2 has a rolling wheel 3 with bodies (not shown) distributed on the perimeter of the rolling wheel 3. On the perimeter, the rolling wheel 3 also has a groove, which cannot be seen from the side, in which a fixed elastic hose 4, 5 is placed. Through section 4 of the hose, rinsing solution is drawn in a rinsing solution flow direction 6, pumped by the rolling wheel 3 and conveyed through section 5 of the hose in the rinsing solution flow direction 7.

From there, the rinsing solution, as an inflow 15, reaches a rinsing solution inlet 14 of an endoscope 10 that for example is a resectoscope, or an endoscope with a monopolar or bipolar HF electrode.

Through a channel (not shown) in the endoscope shaft 12, the rinsing solution enters a body cavity in which the intervention is performed to open the body cavity and, if applicable, to remove dissected tissue or blood, that enters the rinsing solution, through a second rinsing solution channel in the endoscope shaft 12 where it passes as an outflow 17 through a rinsing solution outlet 16 into a receptacle 20 for used rinsing solution. The receptacle 20 comprises a cover 21 and collects the used rinsing solution 22 during the intervention.

At its handle 11, the endoscope 10 is connected to an HF generator 8 to supply the wire loop or HF electrode with current by means of an HF supply line 9.

The rinsing solution pump 2 comprises a measuring apparatus 30 which is designed according to the invention, and which comprises a first measuring apparatus part 31 and a second measuring apparatus part 32. These can be capacitor electrodes of a measuring capacitor whose capacitance is measured which depends on the permittivity of the rinsing solution passing through the hose 5. They can also be probes for a conductivity measurement that measures the conductivity by applying a weak current or a weak voltage, and also differs depending on the rinsing solution. Finally, a measurement of a phase shift between the voltage and current with low-frequency alternating currents can occur, in particular between a few kHz and a few 100 kHz as a consequence of the characteristically slow ionic conduction or conductivity.

The measuring apparatus parts 31 and 32 can also be optical measuring apparatuses such as a UV laser and a UV sensor which measure the intensity of the light passing through the medium. The different solutions have different absorption spectra such that a wavelength can be selected that experiences low absorption in one medium and high absorption in the other medium. Likewise, the different optical density or optical refraction index can be used by measuring refraction such as by using total reflection, wherein the boundary surface of the second measuring apparatus part 32 facing the liquid is a plexiglass pane, a glass pane or a boundary surface with a gas such as air and, in the first measuring apparatus part 31, a light beam is radiated which is subject to total reflection in one type of rinsing solution at the boundary surface to the optically thin medium and therefore does not reach the light-sensitive sensor in the second measuring apparatus part 32, whereas the light in the other rinsing solution is not subject to total reflection at this boundary surface, and hence the light reaches the corresponding sensor in the second measuring apparatus part 32.

Finally, the measuring apparatus can also perform an acoustic measurement, wherein the first measuring apparatus part 31 is then provided as a sonic emitter, and the second measuring apparatus part 32 is provided as a sonic receiver. The radiated sound can be within the ultrasonic range and can comprise a frequency, or a plurality of frequencies, or an entire frequency spectrum. The absorption of high-frequency sound in the media is relatively high such that a distinction can be made between media by the strength of the adsorption, or by the sound level of the unabsorbed sound. Other acoustic measuring methods are to measure a phase difference that arises in the medium from the different speeds of sound from medium to medium, or to measure resonance in a liquid-filled resonance chamber.

The measuring apparatus 30 in FIG. 1 can also contain combinations of these different measuring apparatuses.

The measuring apparatus 30 is connected by means of a signal line 34 to an evaluation apparatus 40 that interprets the measuring results. In the exemplary embodiment according to FIG. 1, this evaluation apparatus 40 is included or arranged within the rinsing solution pump 2. It can however also be a separate apparatus.

The evaluation apparatus 40 analyses the measuring results from the signal line 34 of the measuring apparatus 30 to determine whether the rinsing solution is suitable for the planned intervention or the just performed intervention, and if necessary pursues appropriate countermeasures such as emitting a warning or interrupting the power supply to the electrodes of the endoscopic instrument. The evaluation apparatus 40 is connected by means of a control line 19 to the HF generator 8 which interrupts the HF supply to a signal of the evaluation apparatus 40.

One option for communicating the type of intervention to the evaluation apparatus 40 is manual entry, or connecting to a general operation guidance system such as the Endoalpha system by the applicant in which the corresponding information is saved and which is designed to communicate the information to the evaluation apparatus 40.

Another option is to connect the evaluation apparatus 40 by means of a signal line 18 to the endoscopic instrument 10 such that it can identify itself to the evaluation apparatus 40 and can communicate, if applicable, the mode in which it is operating. This signal line can also be replaced by a signal line to the control apparatus for the endoscopic instrument 10 which also provides this information. Such a control apparatus is an apparatus that normally comprises a data processing system.

By means of the system shown in FIG. 1, in addition to monitoring the use of the suitable rinsing solution by the surgeon or the surgical staff, it is possible to ensure that the patient is safely treated even when the rinsing solution is mixed up.

Figure 2A:
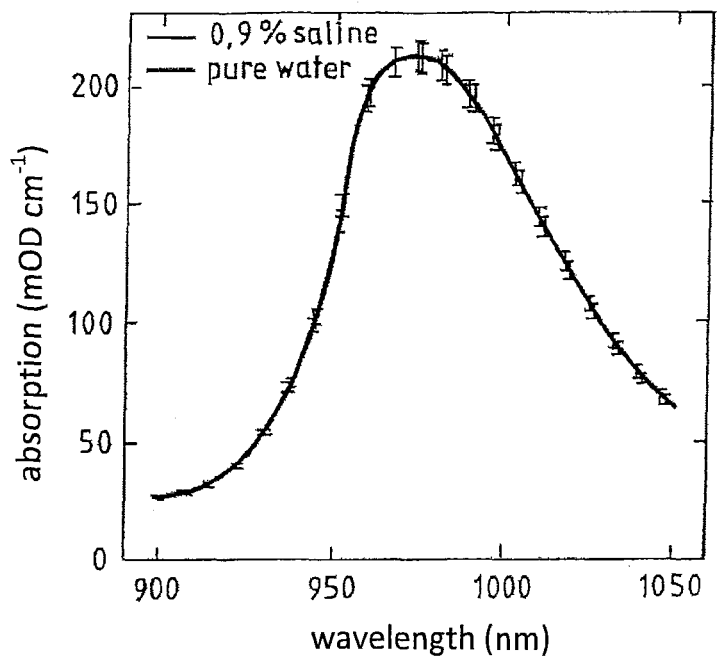
Figure 2B:
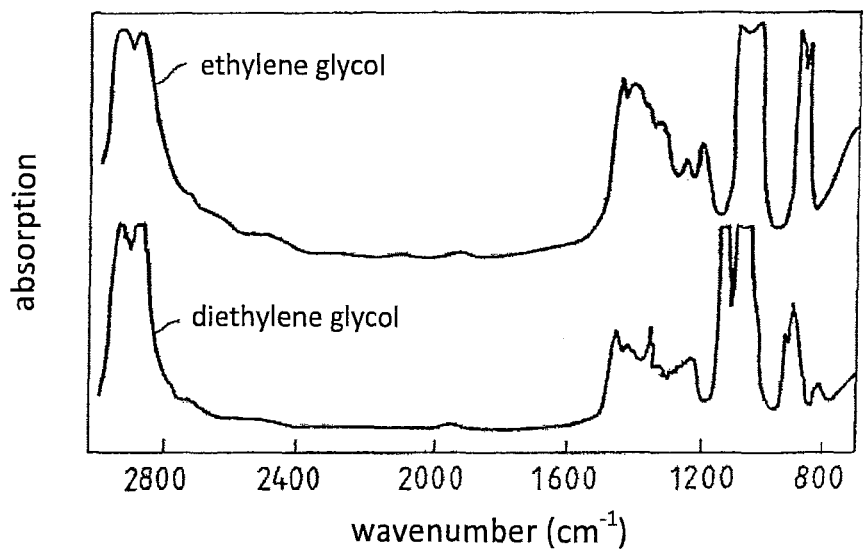

FIGS. 2a and 2b show an example of an absorption spectrum within the infrared range of saline solution (FIG. 2a) and glycols (FIG. 2b). According to FIG. 2a) the 0.9% saline solution manifests maximum absorption within the range of approximately 950 to 1000 nm. This is within the near infrared range.

Contrastingly, glycols such as ethylene glycol and diethylene glycol manifest strong maximum absorptions at wave numbers of approximately 2,900 per cm and within the range between approximately 1,500 to 1,800 per cm. This corresponds to wavelengths of approximately 3,450 nm on the one hand and approximately 6,700 to approximately 11,100 nm on the other hand, i.e. within the distant infrared range. By selecting the wavelengths within one or more of these maximum absorptions, a clear discrimination between saline solution on the one hand and glycol solutions on the other hand can be ascertained. In particular when selecting one of the maximum absorptions of glycol, a clear discrimination is achievable even in an aqueous glycol solution.

Figure 3:
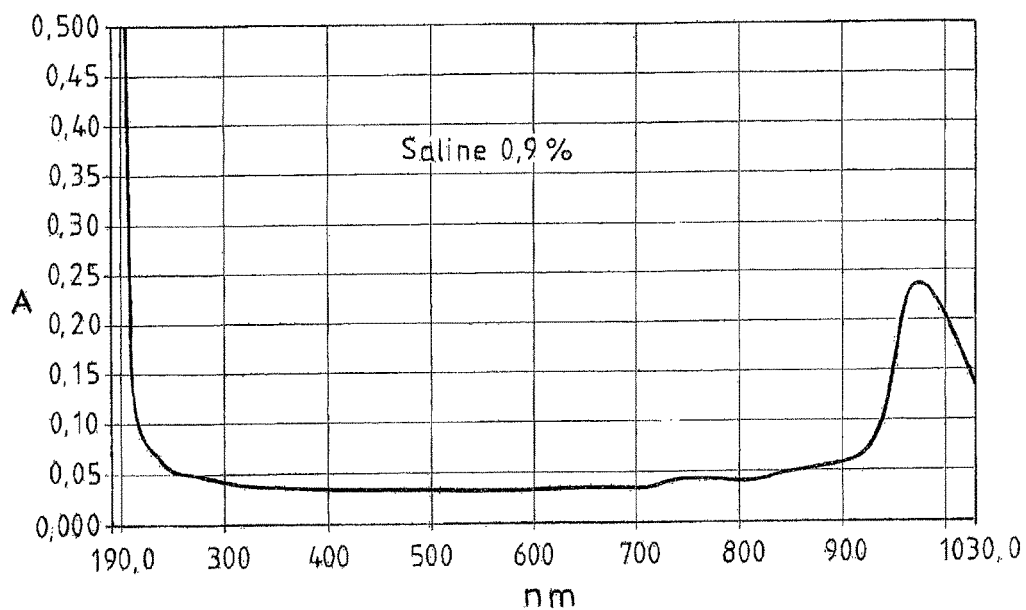
FIGS. 3 and 4 illustrate absorption spectra of saline solution and Purisole® solution.
Figure 4:
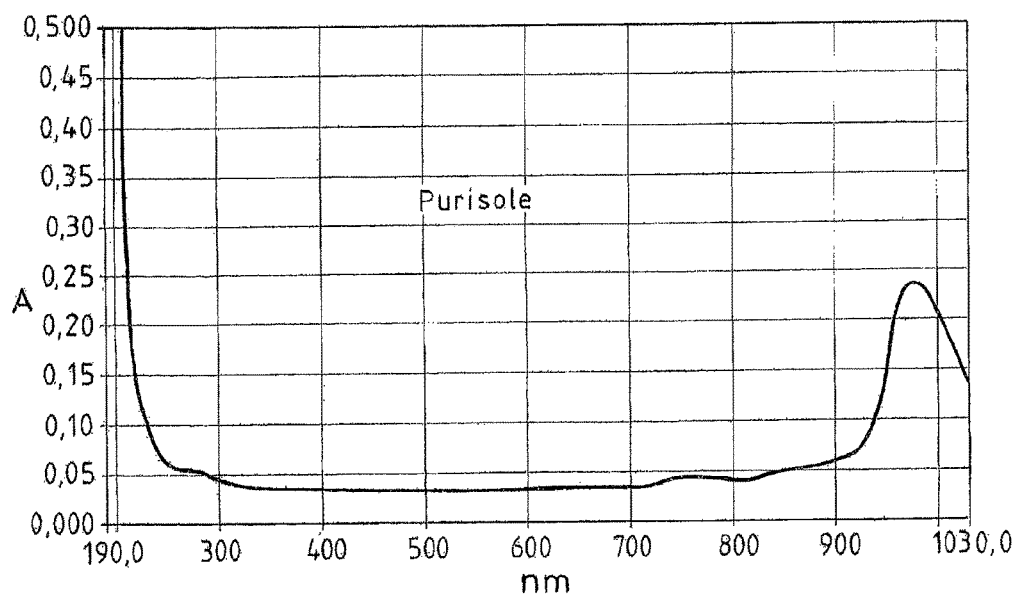

FIGS. 3 and 4 show absorption spectra of saline solution 0.9% and Purisole® solution, the latter being an example of an electrolyte-free solution, within the range between 190 nm and 1030 nm. Differences are revealed particularly within the range between approximately 220 nm and 280 nm, that is within the UV range, where the Purisole® solution reveals a significantly stronger absorption A than the saline solution. A measurement within the UV range is therefore quite effective.

All named features, including those to be taken from the drawings alone, and individual features, which are disclosed in combination with other features, are considered individually and in combination as essential to the invention. Embodiments according to the invention can be realized by the individual features, or a combination of several features.

LIST OF REFERENCE NUMBERS

1 System
2 Rinsing solution pump
3 Rolling wheel
4, 5 Hose
6, 7 Rinsing solution flow
8 HF generator
9 HF supply line
10 Resectoscope
11 Handle
12 Endoscope shaft
14 Rinsing solution inlet
15 Inflow
16 Rinsing solution outlet
17 Outflow
18, 19 Signal line
20 Receptacle
21 Cover
22 Used rinsing solution
30 Measuring apparatus
31 First measuring apparatus part
32 Second measuring apparatus part
34 Signal line
40 Evaluation apparatus

What is claimed is:

1. A system for supplying rinsing solution in endoscopic interventions, the system comprising:
   a rinsing solution pump by means of which the rinsing solution can be conveyed from a rinsing solution supply to an endoscopic instrument;
   a first sensor selected from a group consisting of an electrical sensor, capacitive sensor, optical sensor and an acoustic sensor, the sensor configured to detect at least one material characteristic of the rinsing solution; and
   a computer system configured to determine the type of rinsing solution from the at least one measured material characteristic,
   wherein the first sensor is connected to the computer system, and the computer system is connectable or connected to the endoscopic instrument, the computer system configured to determine a type of required rinsing solution by identifying the endoscopic instrument or its mode and configured to determine whether the rinsing solution is suitable for an intervention to be performed or that has been performed by an endoscopic instrument.

2. The system according to claim 1, wherein the computer system is configured to perform at least one action selected from the group consisting of emit a warning signal when the identified rinsing solution does not correspond to the required solution, and control a high frequency generator to interrupt a health-endangering power supply to parts of the endoscopic instrument.

3. The system according to claim 1, wherein the first sensor is integrated in or on the rinsing solution pump.

4. The system according to claim 1, wherein the computer system is integrated in or on the rinsing solution pump.

5. A rinsing solution pump for supplying rinsing solution in endoscopic interventions, wherein the rinsing solution pump comprises:
- a first sensor selected from a group consisting of an electrical sensor, capacitive sensor, optical sensor and an acoustic sensor, the sensor configured to detect at least one material characteristic of a rinsing solution; and
- a computer system configured to determine the type of rinsing solution from the at least one measured material characteristic to test whether the rinsing solution is suitable for an intervention to be performed or that has been performed by an endoscopic instrument,
- wherein the first sensor is connected to the computer system, and the computer system is connectable or connected to the endoscopic instrument, the computer system configured to determine a type of required rinsing solution by identifying the endoscopic instrument or its mode.

6. The rinsing solution pump according to claim 5, wherein the computer system is configured to perform at least one action selected from the group consisting of emit a warning signal when the identified rinsing solution does not correspond to the required solution and to control a high frequency generator to interrupt a health-endangering power supply to parts of the endoscopic instrument.

* * * * *